United States Patent
Lokireddy

(12) 
(10) Patent No.: US 12,325,860 B2
(45) Date of Patent: Jun. 10, 2025

(54) BACTERIAL EXPRESSION VECTOR FOR ENHANCED PROTEIN SECRETION

(71) Applicant: ONCOSIMIS BIOTECH PRIVATE LIMITED, Hyderabad (IN)

(72) Inventor: Sudarsanareddy Lokireddy, Hyderabad (IN)

( * ) Notice: Subject to any disclaimer, the term of this patent is extended or adjusted under 35 U.S.C. 154(b) by 909 days.

(21) Appl. No.: 17/312,291

(22) PCT Filed: Feb. 15, 2020

(86) PCT No.: PCT/IB2020/051289
§ 371 (c)(1),
(2) Date: Jun. 9, 2021

(87) PCT Pub. No.: WO2020/165874
PCT Pub. Date: Aug. 20, 2020

(65) Prior Publication Data
US 2022/0025383 A1    Jan. 27, 2022

(30) Foreign Application Priority Data
Feb. 15, 2019  (IN) .............................. 201941005938

(51) Int. Cl.
*C12N 15/70* (2006.01)
*C12P 21/02* (2006.01)

(52) U.S. Cl.
CPC .......... *C12N 15/70* (2013.01); *C07K 2319/02* (2013.01); *C12N 2840/002* (2013.01); *C12P 21/02* (2013.01)

(58) Field of Classification Search
CPC .............. C12N 15/70; C12N 2840/002; C07K 2319/02; C07K 2319/20; C07K 2319/61; C12P 21/02; Y02A 50/30
USPC ............................................. 435/69.8, 320.1
See application file for complete search history.

(56) References Cited

U.S. PATENT DOCUMENTS

| 2003/0143685 A1* | 7/2003 | Hu ........................ C12N 15/70 435/348 |
| 2006/0246539 A1 | 11/2006 | Weiner et al. |
| 2009/0148894 A1* | 6/2009 | Broedel ................. C12N 15/67 435/243 |

OTHER PUBLICATIONS

Addgene, Plasmid pGEM5-5Zf(+), Jan. 4, 2015, retrieved on May 25, 2024 from the Internet: <URL: https://web.archive.org/web/20150104201518/https://www.addgene.org/vector-database/2847/>. (Year: 2015).*
Mutoh N, Inokuchi K, Mizushima S. Amino acid sequence of the signal peptide of OmpF, a major outer membrane protein of *Escherichia coli*. FEBS Lett. Jan. 25, 1982;137(2):171-4. (Year: 1982).*
Steigedal M, Valla S. The *Acinetobacter* sp. chnB promoter together with its cognate positive regulator ChnR is an attractive new candidate for metabolic engineering applications in bacteria. Metab Eng. Mar. 2008;10(2):121-9. Epub Sep. 6, 2007. (Year: 2007).*
Taylor-Parker 2016, Addgene Blog, retrieved on May 25, 2024 from the Internet: https://blog.addgene.org/plasmids-101-terminators-and-polya-signals>. (Year: 2016).*
Elena et al. 2014, Frontiers in Microbiology, vol. 5, Article 21, 1-8. (Year: 2014).*

* cited by examiner

*Primary Examiner* — Anne Marie S Wehbe
*Assistant Examiner* — Katie L Pennington

(57) ABSTRACT

The invention provides a bacterial expression vector (100) comprising of a secretory signal sequence in tandem with DNA sequence encoding recombinant protein (103), wherein, the secretory signal sequence is a combination comprising of: a) at least one DNA sequence encoding a signal sequence (101) of gene selected from the group consisting of pelB, ompA, yebF, and ompF, and b) at least one DNA sequence encoding a carrier peptide (102) selected from the group consisting of Seq. ID 5 and 6 encoding truncated yebF.

1 Claim, 6 Drawing Sheets

Specification includes a Sequence Listing.

SEQUENCE LISTING

<160> NUMBER OF SEQ ID NOS: 13

<210> SEQ ID NO 1
<211> LENGTH: 66

```
<212> TYPE: DNA
<213> ORGANISM: Escherichia coli

<400> SEQUENCE: 1
atgaaatacc tgttacctac cgcggctgcg gggctgctgc tgttagcagc tcagccggca    60
atggct                                                                66

<210> SEQ ID NO 2
<211> LENGTH: 63
<212> TYPE: DNA
<213> ORGANISM: Escherichia coli

<400> SEQUENCE: 2
atgaagaaga ccgcgattgc gattgcggtg gcgctggcgg ttttgcgac cgtggcgcag     60 gcg                                                                   63

<210> SEQ ID NO 3
<211> LENGTH: 63
<212> TYPE: DNA
<213> ORGANISM: Escherichia coli

<400> SEQUENCE: 3
atgaaaaagc gtggtgcgtt cctgggcctg ctgctggtta gcgcgtgcgc gagcgtgttt    60
gcg                                                                   63

<210> SEQ ID NO 4
<211> LENGTH: 66
<212> TYPE: DNA
<213> ORGANISM: Escherichia coli

<400> SEQUENCE: 4
atgatgaagc gcaatattct ggcagtgatc gtccctgctc tgttagtagc aggtactgca    60
aacgct                                                                66

<210> SEQ ID NO 5
<211> LENGTH: 99
<212> TYPE: DNA
<213> ORGANISM: Escherichia coli

<400> SEQUENCE: 5
gcgaacaacg aaaccagcaa gagcgtgacc tttccgaaat gcaagatct ggatgcggcg     60 ggtattgcgg cgagcgttaa gcgtgactac cagcaaaac                            99

<210> SEQ ID NO 6
<211> LENGTH: 99
<212> TYPE: DNA
<213> ORGANISM: Escherichia coli

<400> SEQUENCE: 6
gcgaataatg agaccagcaa aagcgtgacc tttccgaagg cggaggacct ggatgcggcg    60
ggtattgcgg cgagcgttaa acgtgactac cagcaaaac                            99

<210> SEQ ID NO 7
<211> LENGTH: 33
<212> TYPE: PRT
<213> ORGANISM: Escherichia coli

<400> SEQUENCE: 7

Ala Asn Asn Glu Thr Ser Lys Ser Val Thr Phe Pro Lys Cys Glu Asp
1               5                   10                  15
```

Leu Asp Ala Ala Gly Ile Ala Ala Ser Val Lys Arg Asp Tyr Gln Gln
            20                  25                  30

Asn

<210> SEQ ID NO 8
<211> LENGTH: 33
<212> TYPE: PRT
<213> ORGANISM: Escherichia coli

<400> SEQUENCE: 8

Ala Asn Asn Glu Thr Ser Lys Ser Val Thr Phe Pro Lys Ala Glu Asp
1               5                   10                  15

Leu Asp Ala Ala Gly Ile Ala Ala Ser Val Lys Arg Asp Tyr Gln Gln
            20                  25                  30

Asn

<210> SEQ ID NO 9
<211> LENGTH: 22
<212> TYPE: PRT
<213> ORGANISM: Escherichia coli

<400> SEQUENCE: 9

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 10
<211> LENGTH: 21
<212> TYPE: PRT
<213> ORGANISM: Escherichia coli

<400> SEQUENCE: 10

Met Lys Lys Arg Gly Ala Phe Leu Gly Leu Leu Leu Val Ser Ala Cys
1               5                   10                  15

Ala Ser Val Phe Ala
            20

<210> SEQ ID NO 11
<211> LENGTH: 21
<212> TYPE: PRT
<213> ORGANISM: Escherichia coli

<400> SEQUENCE: 11

Met Lys Lys Thr Ala Ile Ala Ile Ala Val Ala Leu Ala Gly Phe Ala
1               5                   10                  15

Thr Val Ala Gln Ala
            20

<210> SEQ ID NO 12
<211> LENGTH: 22
<212> TYPE: PRT
<213> ORGANISM: Escherichia coli

<400> SEQUENCE: 12

Met Met Lys Arg Asn Ile Leu Ala Val Ile Val Pro Ala Leu Leu Val
1               5                   10                  15

Ala Gly Thr Ala Asn Ala
            20

<210> SEQ ID NO 13
<211> LENGTH: 6793
<212> TYPE: DNA
<213> ORGANISM: Artificial Sequence
<220> FEATURE:
<223> OTHER INFORMATION: Bacterial expression vector: pBacSec-LC

<400> SEQUENCE: 13

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | ttgacgttgg | agtccacgtt | 300 |
| ctttaatagt | ggactcttgt | tccaaactgg | aacaacactc | aacctatct | cggtctattc | 360 |
| ttttgattta | taagggattt | tgccgatttc | ggcctattgg | ttaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | ccccctatttg | tttattttc | taaatacatt | caaatatgta | 540 |
| tccgctcatg | aattaattct | tagaaaaact | catcgagcat | caaatgaaac | tgcaatttat | 600 |
| tcatatcagg | attatcaata | ccatattttt | gaaaaagccg | tttctgtaat | gaaggagaaa | 660 |
| actcaccgag | gcagttccat | aggatggcaa | gatcctggta | tcggtctgcg | attccgactc | 720 |
| gtccaacatc | aatacaacct | attaatttcc | cctcgtcaaa | aataaggtta | tcaagtgaga | 780 |
| aatcaccatg | agtgacgact | gaatccggtg | agaatggcaa | aagtttatgc | atttctttcc | 840 |
| agacttgttc | aacaggccag | ccattacgct | cgtcatcaaa | atcactcgca | tcaaccaaac | 900 |
| cgttattcat | tcgtgattgc | gcctgagcga | gacgaaatac | gcgatcgctg | ttaaaaggac | 960 |
| aattacaaac | aggaatcgaa | tgcaaccggc | gcaggaacac | tgccagcgca | tcaacaatat | 1020 |
| tttcacctga | atcaggatat | tcttctaata | cctggaatgc | tgttttcccg | gggatcgcag | 1080 |
| tggtgagtaa | ccatgcatca | tcaggagtac | ggataaaatg | cttgatggtc | ggaagaggca | 1140 |
| taaattccgt | cagccagttt | agtctgacca | tctcatctgt | aacatcattg | gcaacgctac | 1200 |
| ctttgccatg | tttcagaaac | aactctggcg | catcgggctt | cccatacaat | cgatagattg | 1260 |
| tcgcacctga | ttgcccgaca | ttatcgcgag | cccatttata | cccatataaa | tcagcatcca | 1320 |
| tgttggaatt | taatcgcggc | ctagagcaag | acgtttcccg | ttgaatatgg | ctcataacac | 1380 |
| cccttgtatt | actgtttatg | taagcagaca | gttttattgt | tcatgaccaa | aatcccttaa | 1440 |
| cgtgagtttt | cgttccactg | agcgtcagac | cccgtagaaa | agatcaaagg | atcttcttga | 1500 |
| gatcctttt | ttctgcgcgt | aatctgctgc | ttgcaaacaa | aaaaaccacc | gctaccagcg | 1560 |
| gtggtttgtt | tgccggatca | agagctacca | actctttttc | cgaaggtaac | tggcttcagc | 1620 |
| agagcgcaga | taccaaatac | tgtccttcta | gtgtagccgt | agttaggcca | ccacttcaag | 1680 |
| aactctgtag | caccgcctac | atacctcgct | ctgctaatcc | tgttaccagt | ggctgctgcc | 1740 |
| agtggcgata | agtcgtgtct | taccgggttg | gactcaagac | gatagttacc | ggataaggcg | 1800 |
| cagcggtcgg | gctgaacggg | gggttcgtgc | acacagccca | gcttggagcg | aacgacctac | 1860 |
| accgaactga | gatacctaca | gcgtgagcta | tgagaaagcg | ccacgcttcc | cgaagggaga | 1920 |
| aaggcggaca | ggtatccggt | aagcggcagg | gtcggaacag | gagagcgcac | gagggagctt | 1980 |
| ccaggggggaa | acgcctggta | tctttatagt | cctgtcgggt | ttcgccacct | ctgacttgag | 2040 |
| cgtcgatttt | tgtgatgctc | gtcagggggg | cggagccat | ggaaaaacgc | cagcaacgcg | 2100 |

-continued

```
gccttttac ggttcctggc cttttgctgg ccttttgctc acatgttctt tcctgcgtta    2160
tccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagactta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccgagagc gctgccggca cctgtcctac    3360
gagttgcatg ataaagaaga cagtcataag tgcggcgacg atagtcatgc ccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggcagact ggaggtggca acgccaatca gcaacgactg tttgccccgcc agttgttgtg    4440
ccacgcggtt gggaatgtaa ttcagctccg ccatcgccgc ttccactttt tcccgcgttt    4500
```

```
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatcta tacgaaacgg    4980
gaatgcggta attacgcttt gttttttataa gtcagatttt aattttttatt ggttaacata    5040 acgaaaggta aaatacataa ggcttactaa aagccagata acagtatgcg tatttgcgcg    5100 ctgattttttg cggtataaga atatatactg atatgtatac ccgaagtatg tcaaaaagag    5160
gtgtgctatg aagcagcgta ttacagtgac agttgacagc gacagctatc agttgctcaa    5220
ggcatatgat gtcaatatct ccggtctggt aagcacaacc atgcagaatg aagcccgtcg    5280
tctgcgtgcc gaacgctgga aagcggaaaa tcaggaaggg atggctgagg tcgcccggtt    5340
tattgaaatg aacggctctt ttgctgacga gaacagggac tggtgaaatg cagtttaagg    5400
tttaccccta taaagagag agccgttatc gtctgtttgt ggatgtacag agtgatatta    5460
ttgacacgcc cgggcgacgg atggtgatcc ccctggccag tgcacgtctg ctgtcagata    5520
aagtctcccg tgaactttac ccggtggtgc atatcgggga tgaaagctgg cgcatgatga    5580
ccaccgatat ggccagtgtg ccggtctccg ttatcgggga agaagtggct gatctcagcc    5640
accgcgaaaa tgcatcaaa aacgccatta acctgatgtt ctggggaata taaatgtcag    5700
gctccgttat acacagccag tctgcagcga tcccgcgaaa tttgacaatt aatcatcggc    5760
tcgtataatg tgtggaattg tgagcggata acaattcccc tctagaaata attttgttta    5820
actttaagaa ggagatatac atatgatgaa acgtaatatc ctggcggtga ttgttccggc    5880
gctgctggtt gcgggcaccg cgaatgcggc gaataatgag accagcaaaa gcgtgacctt    5940
tccgaaggcg gaggacctgg atgcggcggg tattgcggcg agcgttaaac gtgactacca    6000
gcaaaacggt ggcagcggtg gcagcggtag ccaccatcat catcaccaca gcagcggtgg    6060
cagcggtacc gactataagg acgatgacga taaaacgcg gaaggcacct ttaccagcga    6120
tgtgagcagc tacctggagg gtcaagcggc gaaggagttc attgcgtggc tggtgcgtgg    6180
tcgtggctaa tagtgagcgg ccgcggctgt tttggcggat gagagaagat tttcagcctg    6240
atacagatta aatcagaacg cagaagcggt ctgataaaac agaatttgcc tggcggcagt    6300
agcgcggtgg tcccacctga ccccatgccg aactcagaag tgaaacgccg tagcgccgat    6360
ggtagtgtgg ggtctcccca tgcgagagta gggaactgcc aggcatcaaa taaaacgaaa    6420
ggctcagtca aagactggg cctttcgttt tatctgttgt ttgtcggtga acgctctcct    6480
gagtaggaca aatccgccgg gagcggattt gaacgttgcg aagcaacggc ccggagggtg    6540
gcgggcagga cgcccgccat aaactgccag gcatcaaatt aagcagaagg ccatcctgac    6600
ggatggcctt tttgcgtttc tacaaactct ctcgagcacc accaccacca ccactgagat    6660
ccggctgcta acaaagcccg aaaggaagct gagttggctg ctgccaccgc tgagcaataa    6720
ctagcataac cccttggggc ctctaaacgg gtcttgaggg gttttttgct gaaaggagga    6780
actatatccg gat    6793
```

BACTERIAL EXPRESSION VECTOR FOR ENHANCED PROTEIN SECRETION

FIELD OF THE INVENTION

The invention relates to a bacterial expression vector(s) capable of enhanced secretion of recombinant protein in the periplasm space or extracellularly. More specifically, the invention relates to expression vector for expressing and secreting recombinant protein from *Escherichia coli*.

BACKGROUND OF THE INVENTION

Heterologous expression and purification of recombinant proteins in vitro and in vivo represent routine applications of modern molecular biology. Expression of recombinant proteins is typically carried out in prokaryotic host cells, and the microbe *Escherichia coli* have been used regularly for mass production of recombinant proteins, relevant to pharmaceuticals and industrial industries. In view of this, there have been quite a few modifications in host cells to enhance the production of protein of interest in these host cells, using several known methods and mechanisms, to maximize its utility in the industrial production.

The industrial production requires the protein of interest to be secreted out of the host cell for simplifying the purification and down-stream processing of the protein of interest, in a considerable volume. Several efforts are still being made to enhance the extracellular production of target proteins in *Escherichia coli*, by adapting the target cell of expression. One such important adaptation is the use of selected secretory signal peptides, and co-expression of protein of interest along with the secretory signal peptides which assists the translocation of recombinant protein of interest to periplasmic space or extracellular culture media.

Several prior art citations provide novel expression systems for generating protein of interest which are secreted out of host cells:

U.S. Pat. No. 5,583,038A describes expression vectors for expressing and secreting proteins which are heterologous to the bacterium which expresses such proteins wherein such vectors further include DNA encoding at least the secretion signals of lipoproteins designed to achieve lipid acylation and surface expression of heterologous proteins. The bacterial system used is the mycobacteria specifically, and the secretory signal described is mycobacterial lipoprotein secretion signal sequence of Outer Surface Protein A. This expression vector was specifically designed for expressing and secreting an antigen which elicits antibodies against *Borrelia burgdorferi* to be used for treating Lyme disease;

U.S. Pat. No. 5,432,082A describes an expression vector for yeasts which is useful for preparing heterologous proteins, comprising a synthetic oligonucleotide which directs the secretion of the heterologous protein wherein the synthetic oligonucleotide is positioned between the inducible hybrid promoter GAL-CYC and a multiple-site polylinker followed by the signals of transcription termination recognized by the RNA polymerase of the yeasts;

CN101687910A describes a mammalian cell based expression and secretion system. The DNA encoding the signal peptide sequence is selected from: MMRP encoding amino acid sequence [hydrophobic amino] nTSALA DNA sequences or encoded amino acid sequence MKT [hydrophobic amino] nCATVHC DNA sequence, wherein n is an integer between 4-16, the hydrophobic amino acid is A, I, L, M, F or V; and CN107082801A discloses a pelB signal peptide mutant capable of improving the protein secretion efficiency.

Although numerous proteins have been successfully produced by manipulating the secretary method in *Escherichia coli*, still the volume of production is a limiting factor due to proteins not being exported correctly or not exported in a functional state due to aggregation in the cytoplasm; lysis of the cells; incorrect folding; limitations to translocation or proteolytic degradation.

The present invention takes into account the drawbacks of the prior art and provides a novel bacterial expression vector for secretion of recombinant protein extracellularly.

OBJECT OF THE INVENTION

The main object of the invention is to provide a bacterial expression vector carrying a novel secretory signal sequence to direct the secretion of recombinant protein into extracellular media, wherein, the secretory signal sequence is a novel combination of DNA sequence of a signal peptide and DNA sequence of a carrier protein in tandem, and DNA sequence encoding recombinant protein operably linked thereto.

Accordingly, another object of the invention is provide a novel secretory signal sequence for construction of a bacterial expression vector, for enhancing secretion of recombinant protein from the host cells, wherein the secretory signal sequence is a combination of a) at least one DNA sequence encoding a signal sequence of genes selected from the group consisting of pelB represented by Seq. ID 1, ompA represented by Seq. ID 2, yebF represented by Seq. ID 3, and ompF represented by Seq. ID 4, and b) a DNA sequence encoding a carrier protein, preferably, DNA sequence encoding yebf truncated peptide represented by Seq. ID 5 and Seq. ID 6, wherein Seq. ID 6 is generated by mutation of Seq. ID 5.

Yet another object of the invention is provide a system to enhance secretion of recombinant protein from the host cells, more specifically *Escherichia coli*, into the extracellular media.

SUMMARY OF THE INVENTION

In the main embodiment of the present invention, the invention provides a novel bacterial expression vector to enhance secretion of recombinant protein from a host bacterial cells, preferably, *E. coli*, for easy and efficient purification of recombinant protein. Said bacterial expression vector for enhanced secretion of recombinant protein from host bacterial cells, comprising of
- at least one secretory signal sequence,
- at least one gene expression cassette comprising of at least one inducible promoter, an RBS, DNA sequence encoding the recombinant protein, DNA sequence encoding an affinity tag, and at least one gene terminator, with the secretory signal sequence operably linked to the gene expression cassette, and the DNA sequence of the affinity tag operably linked to the DNA sequence of the recombinant protein,
- at least one bacterial ori gene sequence for replication of the vector in the host bacterial cell, and
- at least one DNA sequence for coding a selectable marker with a suitable promoter and a gene terminator sequence flanking the DNA sequence of the selectable marker.

Further, the secretory signal sequence is a combination of:
a) at least one DNA sequence of signal peptide of genes selected from the group consisting of pelB represented by Seq. ID 1 encoding amino acid sequence Seq. ID 9, the DNA sequence of signal peptide ompA represented by Seq. ID 2 encoding amino acid sequence Seq. ID 11, the DNA sequence of signal peptide yebF represented by Seq. ID 3 encoding amino acid sequence Seq. ID 10, and the DNA sequence of signal peptide ompF represented by Seq. ID 4 encoding amino acid sequence Seq. ID 12; and
b) at least one DNA sequence encoding a carrier peptide, preferably, DNA sequence encoding truncated yebF, and the DNA sequence encoding the truncated yebF belongs to the group consisting of Seq. ID 5 and Seq. ID 6, wherein, Seq. ID 5 encodes truncated yebF represented by Seq. ID 7; Seq. ID 6 encodes truncated yebF represented by Seq. ID 8; and the DNA sequence Seq. ID 6 is synthesized by mutating Seq. ID 5, wherein, TGC codon at position 40 in Seq. ID 5 is mutated to GCG codon, to mutate Cys at position 14 of amino acid sequence represented by Seq. ID 7 to Ala at position 14 of amino acid sequence represented by Seq. ID 8.

The bacterial expression vector represented by Seq. ID 13 is 6793 basepair vector comprises of secretory signal sequence, wherein, the secretory signal sequence is a combination of DNA sequence of signal peptide of ompF represented by Seq. ID 4; and truncated yebF peptide encoded by Seq. ID 6.

In yet another embodiment the invention provides a novel bacterial expression vector comprising of at least one affinity tag sequence operably linked to DNA sequence encoding recombinant protein enabling purification of recombinant protein.

In yet another embodiment, the secretory signal sequence is used in conjugation with additional elements in a basic vector that are necessary for its function as a vector including at least one antibiotic selectable marker, and at least one additional selection marker; wherein, the selectable marker is inducible lac operon, and the vector is an inducible vector under lac operon, and is induced by Lactose or Lactose analogues including IPTG.

BRIEF DESCRIPTION OF THE DRAWING

The object of the invention may be understood in more details and more particularly description of the invention briefly summarized above by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

DETAILED DESCRIPTION OF THE INVENTION

Abbreviations used:
pelB refers to: leader DNA sequence encoding the N-terminal amino acid residues of pectatelyase B
ompA refers to: leader DNA sequence encoding the amino acid residues of Outer membrane protein A
ompF refers to: leader DNA sequence encoding the amino acid residues of Outer membrane protein F
yebF refers to: leader DNA sequence encoding the amino acid residues of protein yebF
$Amp^r$/$Kan^r$ refers to: DNA sequence encoding Ampicillin/Kanamycin resistance gene
F1 Ori refers to: Origin of replication
ptac promoter refers to: Promoter for binding RNA polymerase or T7 polymerase
Lac or Lac1 refers to: DNA sequence encodes lac repressor/operon
IPTG refers to: Isopropyl β-d-l-thiogalactopyranoside, inducer of lac operon
Lactose refers to: disaccharide and inducer of lac operon
RBS refers to: Ribosomal binding site
Recombinant protein: Protein of interest encoded by gene cloned in expression vector and expressed in bacterial cells The present invention now will be described hereinafter with reference to the detailed description, in which some, but not all embodiments of the invention are indicated. Indeed, the invention may be embodied in many different forms and should not be construed as limited to the embodiments set forth herein; rather, these embodiments are provided so that this disclosure will satisfy applicable legal requirements. The present invention is described fully herein with non-limiting embodiments and exemplary experimentation.

The present invention relates to a novel bacterial expression vector to enhance secretion of recombinant protein from a host bacterial cells, preferably, E. coli, for easy and efficient purification of the recombinant protein.

Figure 1:
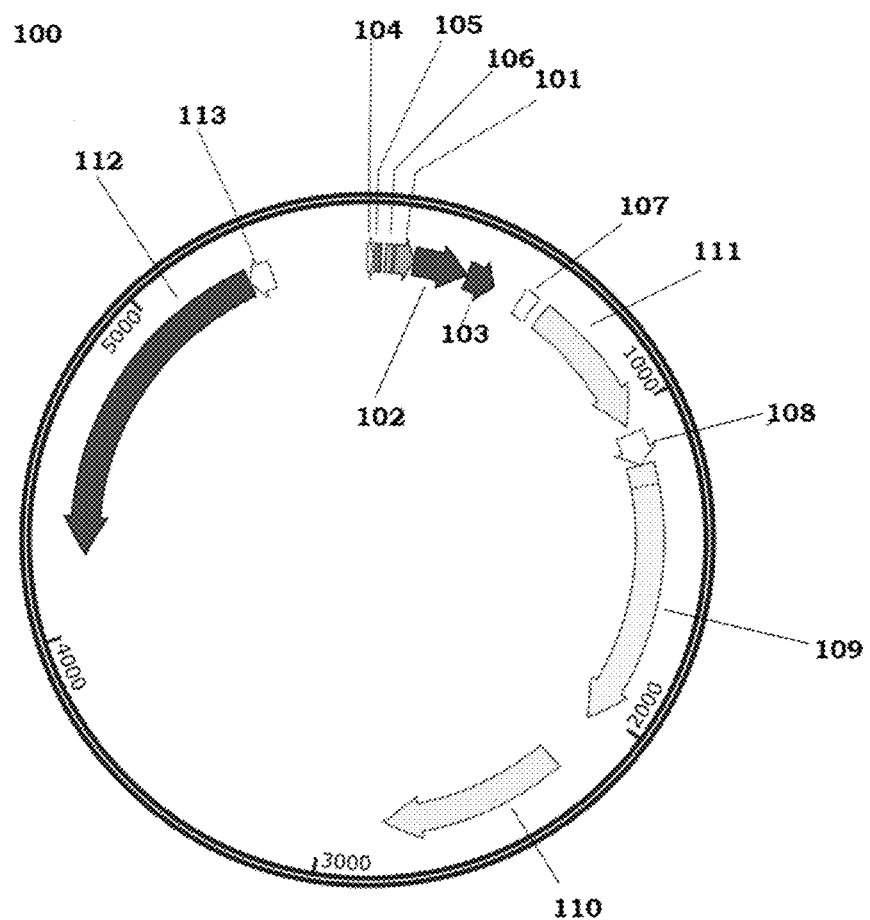
FIG. 1 is a schematic representation of a novel bacterial expression vector comprising of combination of secretory signal sequences for enhancing secretion of protein/peptide of interest outside the host cells.

In the main embodiment, the invention provides a bacterial expression vector (100), as depicted FIG. 1, comprising of a secretory signal sequence in tandem with DNA sequence encoding recombinant protein (103), wherein, the secretory signal sequence is a combination comprising of:
a) at least one DNA sequence encoding a signal sequence (101) of genes selected from the group consisting of pelB represented by Seq. ID 1 encoding amino acid sequence Seq. ID 9, ompA represented by Seq. ID 2 encoding amino acid sequence Seq. ID 11, yebF represented by Seq. ID 3 encoding amino acid sequence Seq. ID 10, and ompF represented by Seq. ID 4 encoding amino acid sequence Seq. ID 12, and
b) at least one DNA sequence encoding a carrier peptide (102), preferably, DNA sequence encoding truncated yebF represented by Seq. ID 5 and Seq. ID 6.

Seq. ID 5 encodes for 33 amino acid carrier peptide represented by Seq. ID 7, and Seq. ID 6 encodes for peptide represented by Seq. 8.

the DNA sequence Seq. ID 6 is synthesized by mutating Seq. ID 5, wherein, TGC codon at position 40 in Seq. ID 5 is mutated to GCG codon, to mutate Cys at position 14 of Seq. ID 7 to Ala at position 14 of Seq. ID 8.

Table 1 provides the DNA sequence encoding the signal sequence or the carrier peptides

| SEQ. ID No. | DNA sequence |
|---|---|
| 1 | ATGAAATACCTGTTACCTACCGCGGCTGCGGGGCTGCTGCTGTTAGCAGCTCAGCCGGCAATGGCT |
| 2 | ATGAAGAAGACCGCGATTGCGATTGCGGTGGCGCTGGCGGGTTTTGCGACCGTGGCGCAGGCG |
| 3 | ATGAAAAAGCGTGGTGCGTTCCTGGGCCTGCTGCTGGTTAGCGCGTGCGCGAGCGTGTTTGCG |
| 4 | ATGATGAAGCGCAATATTCTGGCAGTGATCGTCCCTGCTCTGTTAGTAGCAGGTACTGCAAACGCT |
| 5 | GCGAACAACGAAACCAGCAAGAGCGTGACCTTTCCGAAATGCGAAGATCTGGATGCGGCGGGTATTGCGGCGAGCGTTAAGCGTGACTACCAGCAAAAC |
| 6 | GCGAATAATGAGACCAGCAAAAGCGTGACCTTTCCGAAGGCGGAGGACCTGGATGCGGCGGGTATTGCGGCGAGCGTTAAACGTGACTACCAGCAAAAC |

| | Peptide Sequence |
|---|---|
| 7 | ANNETSKSVTFPKCEDLDAAGIAASVKRDYQQN |
| 8 | ANNETSKSVTFPKAEDLDAAGIAASVKRDYQQN |
| 9 | MKYLLPTAAAGLLLLAAQPAMA |
| 10 | MKKRGAFLGLLLVSACASVFA |
| 11 | MKKTAIAIAVALAGFATVAQA |
| 12 | MMKRNILAVIVPALLVAGTANA |

| | Vector Sequence |
|---|---|
| 13 | TGGCGAATGGGACGCGCCCTGTAGCGGCGCATTAAGCGCGGCGGGTGTGGTGGTTACGCGCAGCGTGACCGCTACACTTGCCAGCGCCCTAGCGCCCGCTCCTTTCGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCACCTCGACCCCAAAAAACTTGATTAGGGTGATGGTTCACGTAGTGGGCCATCGCCCTGATGACGGTTTTTCGCCCTTTGACGTTGGAGTCCACGTTCTTTAATAGTGGACTCTTGTTCCAAACTGGAACAACACTCAACCCTATCTCGGTCTATTCTTTTGATTTATAAGGGATTTTGCCGATTTCGGCCTATTGGTTAAAAAATGAGCTGATTTAACAAAAATTTAACGCGAATTTTAACAAAATATTAACGTTTACAATTTCAGGTGGCACTTTTCGGGGAAATGTGCGCGGAACCCCTATTTGTTTATTTTTCTAAATACATTCAAATATGTATCCGCTCATGAATTAATTCTTAGAAAAACTCATCGAGCATCAAATGAAACTGCAATTTATTCATATCAGGATTATCAATACCATATTTTTGAAAAAGCCGTTTCTGTAATGAAGGAGAAAACTCACCGAGGCAGTTCCATAGGATGGCAAGATCCTGGTATCGGTCTGCGATTCCGACTCGTCCAACATCAATACAACCTATTAATTTCCCCTCGTCAAAAATAAGGTTATCAAGTGAGAAATCACCATGAGTGACGACTGAATCCGGTGAGAATGGCAAAAGTTTATGCATTTCTTTCCAGACTTGTTCAACAGGCCAGCCATTACGCTCGTCATCAAAATCACTCGCATCAACCAAACCGTTATTCATTCGTGATTGCGCCTGAGCGAGACGAAATACGCGATCGCTGTTAAAAGGACAATTACAAACAGGAATCGAATGCAACCGGCGCAGGAACACTGCCAGCGCATCAACAATATTTTCACCTGAATCAGGATATTCTTCTAATACCTGGAATGCTGTTTTCCCGGGATCGCAGTGGTGAGTAACCATGCATCATCAGGAGTACGGATAAAATGCTTGATGGTCGGAAGAGGCATAAATTCCGTCAGCCAGTTTAGTCTGACCATCTCATCTGTAACATCATTGGCAACGCTACCTTTGCCATGTTTCAGAAACAACTCTGGCGCATCGGGCTTCCCATACAATCGATAGATTGTCGCACCTGATTGCCCGACATTATCGCGAGCCCATTTATACCCATATAAATCAGCATCCATGTTGGAATTTAATCGCGGCCTAGAGCAAGACGTTTCCCGTTGAATATGGCTCATAACACCCCTTGTATTACTGTTTATGTAAGCAGACAGTTTTATTGTTCATGACCAAAATCCCTTAACGTGAGTTTTCGTTCCACTGAGCGTCAGACCCCGTAGAAAAGATCAAAGGATCTTCTTGAGATCCTTTTTTTCTGCGCGTAATCTGCTGCTTGCAAACAAAAAAACCACCGCTACCAGCGGTGGTTTGTTTGCCGGATCAAGAGCTACCAACTCTTTTTCCGAAGGTAACTGGCTTCAGCAGAGCGCAGATACCAAATACTGTCCTTCTAGTGTAGCCGTAGTTAGGCCACCACTTCAAGAACTCTGTAGCACCGCCTACATACCTCGCTCTGCTAATCCTGTTACCAGTGGCTGCTGCCAGTGGCGATAAGTCGTGTCTTACCGGGTTGGACTCAAGACGATAGTTACCGGATAAGGCGCAGCGGTCGGGCTGAACGGGGGGTTCGTGCACACAGCCCAGCTTGGAGCGAACGACCTACACCGAACTGAGATACCTACAGCGTGAGCTATGAGAAAGCGCCACGCTTCCCGAAGGGAGAAAGGCGGACAGGTATCCGGTAAGCGGCAGGGTCGGAACAGGAGAGCGCACGAGGGAGCTTCCAGGGGAAACGCCTGGTATCTTTATAGTCCTGTCGGGTTTCGCCACCTCTGACTTGAGCGTCGATTTTTGTGATGCTCGTCAGGGGGGCGGAGCCTATGGAAAAACGCCAGCAACGCGGCCTTTTTACGGTTCCTGGCCTTTTGCTGGCCTTTTGCTCACATGTTCTTTCCTGCGTTATCCCCTGATTCTGTGGATAACCGTATTACCGCCTTTGAGTGAGCTGATACCGCTCGCCGCAGCCGAACGACCGAGCGCAGCGAGTCAGTGAGCGAGGAAGCGGAAGAGCGCCTGATGCGGTATTTTCTCCTTACGCATCTGTGCGGTATTTCACACCGCATATATGGTGCACTCTCAGTACAATCTGCTCTGATGCCGCATAGTTAAGCCAGTATACACTCCGCTATCGCTACGTGACTGGGTCATGGCTGCGCCCCGACACCCGCCAACACCCGCTGACGCGCCCTGACGGGCTTGTCTGCTCCCGGCATCCGCTTACAGACAAGCTGTGACCGTCTCCGGGAGCTGCATGTGTCAGAGGTTTCACCGTCATCACCGAAACGCGCGAGGCAGCTGCGGTAAAGCTCATCAGCGTGGTCGTGAAGCGATTCACAGATGTCTGCCTGTTCATCCGCGTCCAGCTCGTTGAGTTTCTCCAGAAGCGTTAATGTCTGGCTTCTGATAAAGCGGGCCATGTTAAGGGCGGTTTTTTCCTGTTTGGTCACTGATGCCTCCGTGTAAGGGGGATTTCTGTTCATGGGGGTAATGATACCGATGAAACGAGAGAGGATGCTCACGATACGGGTTACTGATGATGAACATGCCCGGTTACTGGAACGTTGTGAGGGTAAACAACTGGCGGTATGGATGCGGCGGGACCAGAGAAAAATCACTCAGGGTCAATGCCAGCGCTTCGTTAATACAGATGTAGGTGTTCCACAGGGTAGCCAGCAGCATCCTGCGATGCAGATCCGGAACATAATGGTGCAGGGCGCTGACTTCCGCGTTTCCAGACTTTACGAAACACGGAAACCGAAGACCATTCATGTTGTTGCTCAGGTCGCAGACGTTTTGCAGCAGCAGTCGCTTCACGTTCGCTCGCGTATCGGTGATTCATTCTGCTAACCAGTAAGGCAACCCCGCCAGCCTAGCCGGGTCCTCAACGACAGGAGCACGATCATGCGCACCCGTGGGGCCGCCATGCCGGCGATAATGGCCTGCTTCTCGCCGAAACGTTTGGTGGCGGGACCAGTGACGAAGGCTTGAGCGAGGGCGTGCAAGATTCCGAATACCGCAAGCGACAGGCCGATCATCGTCGCGCTCCAGCGAAAGCGGTCCTCGCCGAAAATGACCCAGAGCGCTGCCGGCACCTGTCCTACGAGTTGCATGATAAAGAAGACAGTCATAAGTGCGGCGACGATAGTCATGCCCCGCGCCCACCGGAAGGAGCTGACTGGGTTGAAGGCTCTCAAGGGCATCGGTCGAGATCCCGGTGCCTAATGAGTGAGCTAACTTACATTAATTGCGTTGCGCTCACTGCCCGCTTTCCAGTCGGGAAACCTGTCGTGCCAGCTGCATTAATGAATCGGCCAACGCGCGGGGAGAGGCGGTTTGCGTATTGGGCGCCAGGGTGGTTTTCTTTTCACCAGTGAGACGGGCAACAGCTGATTGCCCTTCACCGCCTGGCCCTGAGAGAGTTGCAGCAAGCGGTCCACGCTGGTTTGCCCCAGCAGGCGAAAATCCTGTTTGATGGTGGTTAACGGCGGGATATAACATGAGCTGTCTTCGGTATCGTCGTATCCCACTACCGAGATATCCGCACCAACGCGCAGCCCGGACTCGGTAATGGCGCGCATTGCGCCCAGCGCCATCTGATCGTTGGCAACCAGCATCGCAGTGGGAACGATGCCCTCATTCAGCATTTGCATGGTTTGTTGAAACCGGACATGGCACTCCAGTCGCCTTCCCGTTCCGCTAT |

-continued

| SEQ. ID No. | |
|---|---|
| | CGGCTGAATTTGATTGCGAGTGAGATATTTATGCCAGC
CAGCCAGACGCAGACGCGCCGAGACAGAACTTAATGG
GCCCGCTAACAGCGCGATTTGCTGGTGACCCAATGCGA
CCAGATGCTCCACGCCCAGTCGCGTACCGTCTTCATGG
GAGAAAATAATACTGTTGATGGGTGTCTGGTCAGAGAC
ATCAAGAAATAACGCCGGAACATTAGTGCAGGCAGCTT
CCACAGCAATGGCATCCTGGTCATCCAGCGGATAGTTA
ATGATCAGCCCACTGACGCGTTGCGCGAGAAGATTGTG
CACCGCCGCTTTACAGGCTTCGACGCCGCTTCGTTCTAC
CATCGACACCACCACGCTGGCACCCAGTTGATCGGCGC
GAGATTTAATCGCCGCGACAATTTGCGACGGCGCGTGC
AGGGCCAGACTGGAGGTGGCAACGCCAATCAGCAACG
ACTGTTTGCCCGCCAGTTGTTGTGCCACGCGGTTGGGA
ATGTAATTCAGCTCCGCCATCGCCGCTTCCACTTTTTCC
CGCGTTTTCGCAGAAACGTGGCTGGCCTGGTTCACCAC
GCGGGAAACGGTCTGATAAGAGACACCGGCATACTCT
GCGACATCGTATAACGTTACTGGTTTCACATTCACCACC
CTGAATTGACTCTCTTCCGGGCGCTATCATGCCATACCG
CGAAAGGTTTTGCGCCATTCGATGGTGTCCGGGATCTC
GACGCTCTCCCTTATGCGACTCCTGCATTAGGAAGCAG
CCCAGTAGTAGGTTGAGGCCGTTGAGCACCGCCGCCGC
AAGGAATGGTGCATGCAAGGAGATGGCGCCCAACAGT
CCCCCGGCCACGGGGCCTGCCACCATACCCACGCCGAA
ACAAGCGCTCATGAGCCCGAAGTGGCGAGCCCGATCTT
CCCCATCGGTGATGTCGGCGATATAGGCGCCAGCAACC
GCACCTGTGGCGCCGGTGATGCCGGCCACGATGCGTCC
GGCGTAGAGGATCGAGATCTATACGAAACGGGAATGC
GGTAATTACGCTTTGTTTTTATAAGTCAGATTTTAATTTT
TATTGGTTAACATAACGAAAGGTAAAATACATAAGGCT
TACTAAAAGCCAGATAACAGTATGCGTATTTGCGCGCT
GATTTTTGCGGTATAAGAATATATACTGATATGTATACC
CGAAGTATGTCAAAAAGAGGTGTGCTATGAAGCAGCG
TATTACAGTGACAGTTGACAGCGACAGCTATCAGTTGC
TCAAGGCATATGATGTCAATATCTCCGGTCTGGTAAGC
ACAACCATGCAGAATGAAGCCCGTCGTCTGCGTGCCGA
ACGCTGGAAAGCGGAAAATCAGGAAGGGATGGCTGAG
GTCGCCCGGTTTATTGAAATGAACGGCTCTTTTGCTGAC
GAGAACAGGGACTGGTGAAATGCAGTTTAAGGTTTAC
ACCTATAAAAGAGAGAGCCGTTATCGTCTGTTTGTGGA
TGTACAGAGTGATATTATTGACACGCCCGGGCGACGGA
TGGTGATCCCCCTGGCCAGTGCACGTCTGCTGTCAGAT
AAAGTCTCCCGTGAACTTTACCCGGTGGTGCATATCGG
GGATGAAAGCTGGCGCATGATGACCACCGATATGGCC
AGTGTGCCGGTCTCCGTTATCGGGGAAGAAGTGGCTG
ATCTCAGCCACCGCGAAAATGACATCAAAAACGCCATT
AACCTGATGTTCTGGGGAATATAAATGTCAGGCTCCGT
TATACACAGCCAGTCTGCAGCGATCCCGCGAAATTTGA
CAATTAATCATCGGCTCGTATAATGTGTGGAATTGTGA
GCGGATAACAATTCCCCTCTAGAAATAATTTTGTTTAAC
TTTAAGAAGGAGATATACATATGATGAAACGTAATATC
CTGGCGGTGATTGTTCCGGCGCTGCTGGTTGCGGGCAC
CGCGAATGCGGCGAATAATGAGACCAGCAAAAGCGTG
ACCTTTCCGAAGGCGGAGGACCTGGATGCGGCGGGTA
TTGCGGCGAGCGTTAAACGTGACTACCAGCAAAACGGT
GGCAGCGGTGGCAGCGGTAGCCACCATCATCATCACCA
CAGCAGCGGTGGCAGCGGTACCGACTATAAGGACGAT
GACGATAAACACGCGGAAGGCACCTTTACCAGCGATGT
GAGCAGCTACCTGGAGGGTCAAGCGGCGAAGGAGTTC
ATTGCGTGGCTGGTGCGTGGTCGTGGCTAATAGTGAGC
GGCCGCGGCTGTTTTGGCGGATGAGAGAAGATTTTCAG
CCTGATACAGATTAAATCAGAACGCAGAAGCGGTCTGA
TAAAACAGAATTTGCCTGGCGGCAGTAGCGCGGTGGTC
CCACCTGACCCCATGCCGAACTCAGAAGTGAAACGCCG
TAGCGCCGATGGTAGTGTGGGGTCTCCCCATGCGAGA
GTAGGGAACTGCCAGGCATCAAATAAAACGAAAGGCT
CAGTCGAAAGACTGGGCCTTTCGTTTTATCTGTTGTTTG
TCGGTGAACGCTCTCCTGAGTAGGACAAATCCGCCGGG
AGCGGATTTGAACGTTGCGAAGCAACGGCCCGGAGGG
TGGCGGGCAGGACGCCCGCCATAAACTGCCAGGCATC
AAATTAAGCAGAAGGCCATCCTGACGGATGGCCTTTTT
GCGTTTCTACAAACTCTCTCGAGCACCACCACCACCACC
ACTGAGATCCGGCTGCTAACAAAGCCCGAAAGGAAGC
TGAGTTGGCTGCTGCCACCGCTGAGCAATAACTAGCAT
AACCCCTTGGGGCCTCTAAACGGGTCTTGAGGGGTTTT
TTGCTGAAAGGAGGAACTATATCCGGAT |

In another embodiment, the bacterial expression vector further comprises of at least one gene expression cassette comprising of at least one inducible promoter, an RBS, DNA sequence encoding the recombinant protein, DNA sequence encoding an affinity tag, and at least one gene terminator, with the secretory signal sequence operably linked to the gene expression cassette, and the DNA sequence of the affinity tag is operably linked to the DNA sequence of the recombinant protein. The bacterial expression vector additionally comprises of at least one multiple cloning site (MSC) to enable cloning of DNA sequence of recombinant protein under the promoter.

In yet another embodiment, the bacterial expression vector further comprises of at least one antibiotic resistance gene and at least one additional selection marker each controlled by a respective gene promoter.

In yet another embodiment, the bacterial expression vector comprises of at least one ori sequence for enabling replication of expression vector in the host cells.

Figure 2:
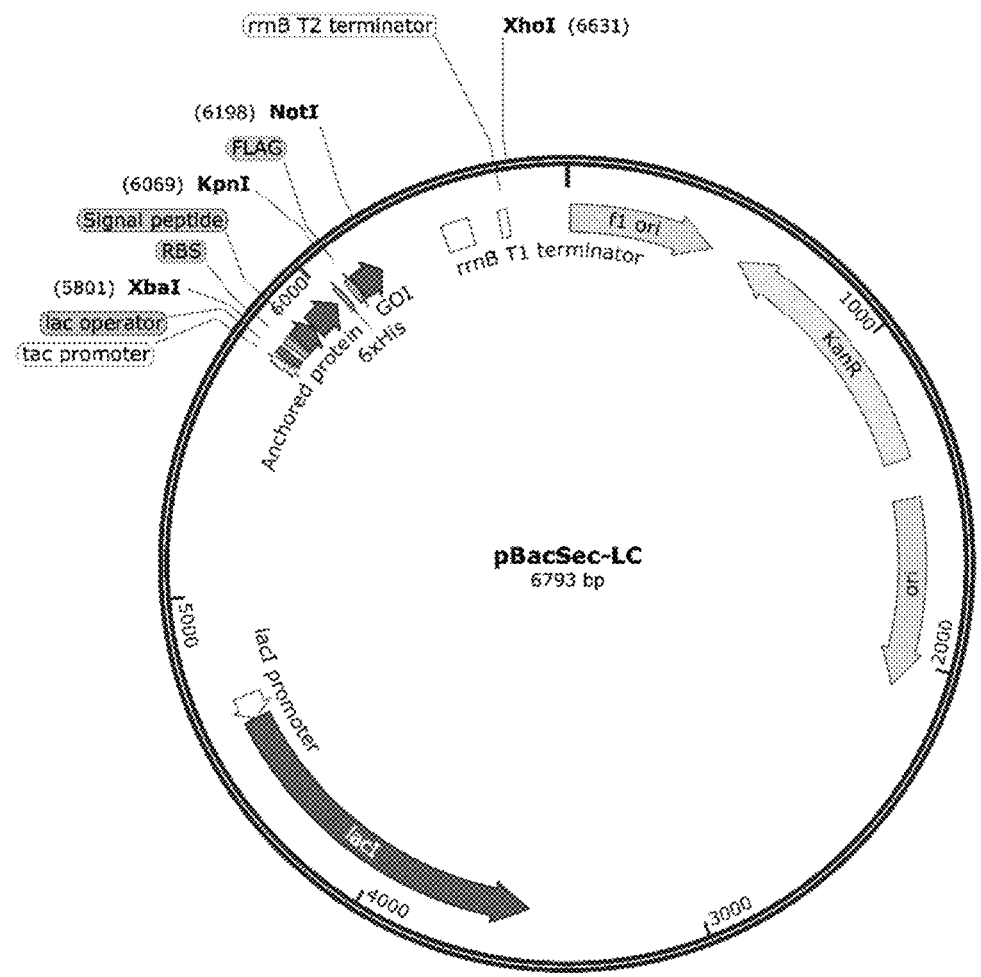
FIG. 2 is a schematic representation of pBacSec-LC vector.

In yet another embodiment, the bacterial expression vector, pBacSec-LC, with the vector being inducible under lac operon, and is induced by Lactose or Lactose analogues including IPTG. As depicted in FIG. 2, the novel bacterial expression vector, pBacSec-LC, is of around 6793 basepairs comprising of secretory signal sequence for efficient and enhanced secretion of recombinant protein which is in tandem with the secretory signal sequence. The pBacSec-LC vector comprises of:

tac promoter and lac operator as inducible promoter;
an RBS;
a secretory signal sequence which is a combination of signal sequence of the gene selected from the group consisting of DNA sequence represented by Seq. ID 1-4, and a DNA sequence represented by Seq. ID 5 or Seq. ID 6;
DNA sequence encoding 6-His tag and FLAG tag which are affinity tags;
DNA sequence encoding recombinant protein;
a gene terminator for transcriptional termination of recombinant protein;
an ori sequence to enable replication of vector in E. coli;
a lac operon as a selectable marker for blue-white recombinant colony selection; and
a kanamycin resistance gene as an antibiotic selectable marker.

The pBacSec-LC vector represented Seq. ID 13 comprises of secretory signal sequence which is a combination of the DNA sequence encoding signal sequence of the gene ompF represented by Seq. ID 4 and the DNA sequence encoding the truncated yebF represented by Seq. ID 6.

Example 1

Secretory Efficiency of Different Combinations of Signal Sequence and Carrier Peptide A. Luciferase Assay:
E. coli strains, NEB 5-alpha and BL21(DE3) were used for transformation and luciferase assay.
Different combinations of secretory signals were constructed such as:
a) signal sequence of Seq. ID 1 and carrier protein represented by Seq. ID 5,
b) signal sequence of Seq. ID 2 and carrier protein represented by Seq. ID 5,
c) signal sequence of Seq. ID 3 and carrier protein represented by Seq. ID 5, and d) signal sequence of Seq. ID 4 and carrier protein represented by Seq. ID 5.

Gaussia luciferase were used as reporter system for the examination of secretory activity of E. coli. Guassian luciferase assays were performed using Pierce Gaussia Luciferase glow assay kit. Media was collected at indicated time intervals from culture after induction and luciferase activity measured from media as described in manufacturer's protocol.

Figure 3:
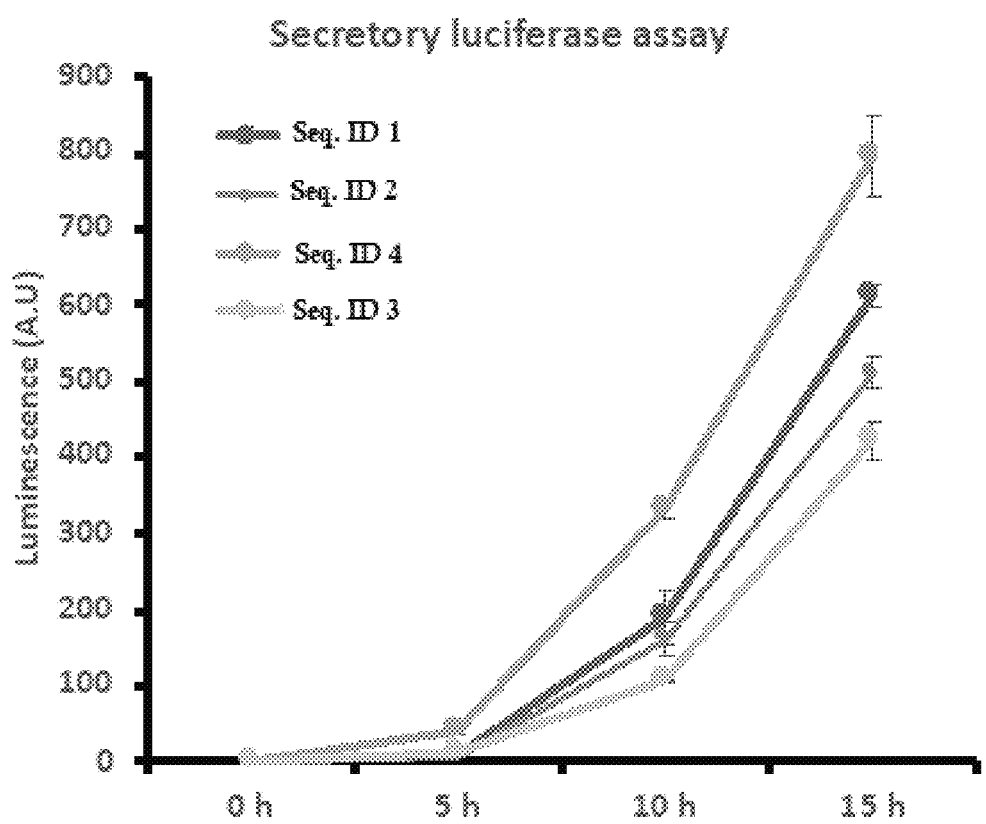
FIG. 3 is a graphical representation of comparative efficiencies of Seq. ID 1, Seq. ID 2, Seq. ID 3, and Seq. ID 4 using Gaussian luciferase assay.

As depicted in FIG. 3, combination of every signal peptide with Seq. ID 5 shows secretion amongst which combination of signal peptide of ompF represented by Seq. ID 4 with carrier protein Seq. ID 5 showed better secretory efficiency.

B. Efficiency of Secretion of Peptides Ranging from 5-20 kDa
  i. Construct of expression vector: DNA sequences of recombinant protein encoding peptides of 5, 10, 15, and 20 kDa were cloned in pBacSec-LC vector having secretory signal sequence comprising of Seq. ID 4 and Seq. ID 6.
  ii. Preparation of starter culture: 3 ml of autoclaved growth media having pH of 6.90 is taken in sterile snap cap tube. Single CFU picked from Luria-Bertani agar plate and inoculated aseptically into growth media and incubated overnight at 37° C. with 225 rpm in rotatory incubator.
  iii. Shake flask culturing: 1 ml of overnight starter culture is inoculated into 25 ml of growth media (1:25 dilutions) having pH of 6.90 taken in 250 ml baffled flask. Flasks were incubated in rotatory shaker incubator maintained at 37° C., 225 rpm. After 4 hours of incubation OD600 reached ~1.8 to 2.0. Cells were induced with 0.2 mM Isopropyl β-d-l-thiogalactopyranoside (IPTG), and inducer of lac operon. Post induction, supplements such as glycine, glutamic acid, arginine, reduced glutathione were added. Samples were collected hourly post induction i.e 300 µL of culture, centrifuged at 14K rpm for 3 minutes to separate cells and media to check expression and secretion of protein. The cells were lysed to form the lysate. Cell lysate and media components were compared for presence of recombinant peptides.
  iv. SDS-PAGE: SDS-PAGE was used to analyze the heterologous gene expression of desired recombinant protein from culture media post-induction.

Figure 4:
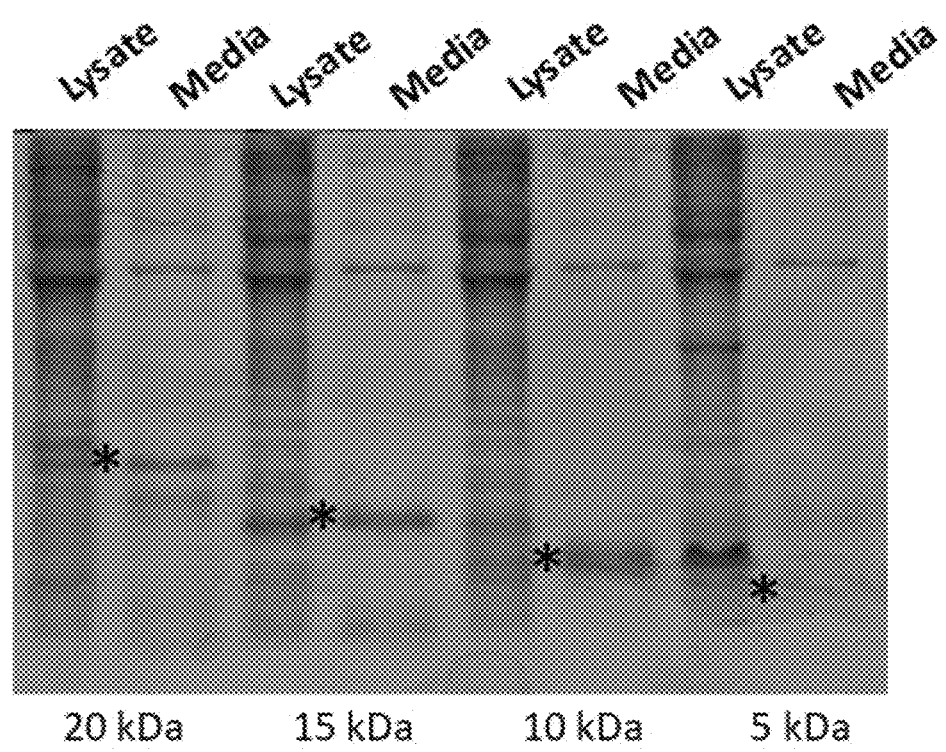
FIG. 4 is pictorial representation of SDS-PAGE gel with lysates or media component of bacterial cell culture expressing pBacSec-LC vector having secretory signal sequence comprising of Seq. ID 4 and Seq. ID 6.

As depicted in FIG. 4, recombinant peptides of size 5-20 kDa were seen to present in the media component more than the cell lysates clearly indicating secretion of the recombinant peptide. And all the peptides ranging from 5-20 kDa were equally secreted with similar efficiency indicating that the secretory sequence was capable to secrete peptides in the range of 5-20 kDa.

C. The Yield of Recombinant Protein

DNA sequence of recombinant protein was cloned in pBacSec-LC vector with Seq. ID 13, and transformed in E. coli. The E. coli starter culture was prepared and then upscaled further as described earlier under section B of example 1. The E. coli culture was induced with 0.2 mM IPTG for recombinant protein expression, and amount of recombinant protein secreted was measured after different time intervals of induction by IPTG.

Figure 5:
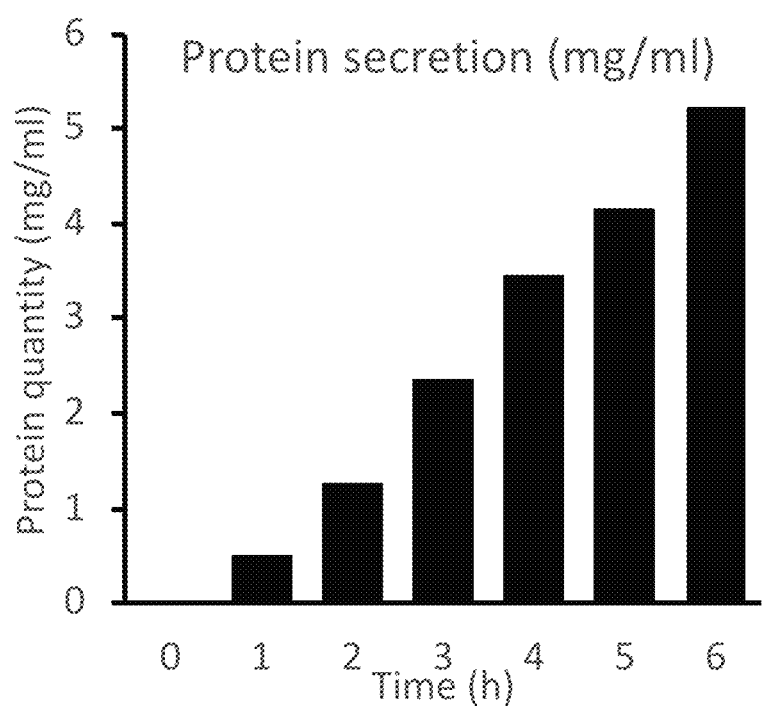
FIG. 5 is a graphical representation of yield of recombinant protein after time points of induction by IPTG.

As depicted in FIG. 5, the yield of the recombinant protein after 1 hour of induction is around 0.5 g/L, and after 6 hours the yield of the recombinant protein reaches more than 5 g/l. The yield of the recombinant protein consistently increases after every hour of induction. This suggests that the bacterial secretory technology enables cells to devout maximum resources in protein expression and secretion upon induction after desired cell density is attained. After first hour of induction recombinant protein is secreted into media without stunting cell proliferation mechanism.

Example 2

Secretory Efficiency of Seq. Id 6 Compared to Seq. Id 5

DNA sequences of recombinant protein were cloned in pBacSec-LC vector having secretory signal sequence comprising of combination of Seq. ID 4 and Seq. ID 5, or Seq. ID 4 and Seq. ID 6.

Seq. ID 6 is synthesized by mutating Seq. ID 5, wherein, TGC codon at position 40 of Seq. ID 5 is mutated to GCG codon in Seq. ID 6, to mutate Cys at position 14 of Seq. ID 7 to Ala in Seq. ID 8. The Cys residue at position 14 of the peptide enables dimerization and increases the chances of development of inclusion bodies. Mutation of Cys to Ala, abrogates the property of dimerization of the peptide thereby reducing the chances of formation of inclusion bodies which in turn should enhance secretion of the peptide and the recombinant peptide.

The E. coli cells were transformed with respective vectors and two sets of cultures were prepared under reducing and non-reducing conditions and induction was carried out using IPTG for peptide secretion.

Figure 6:
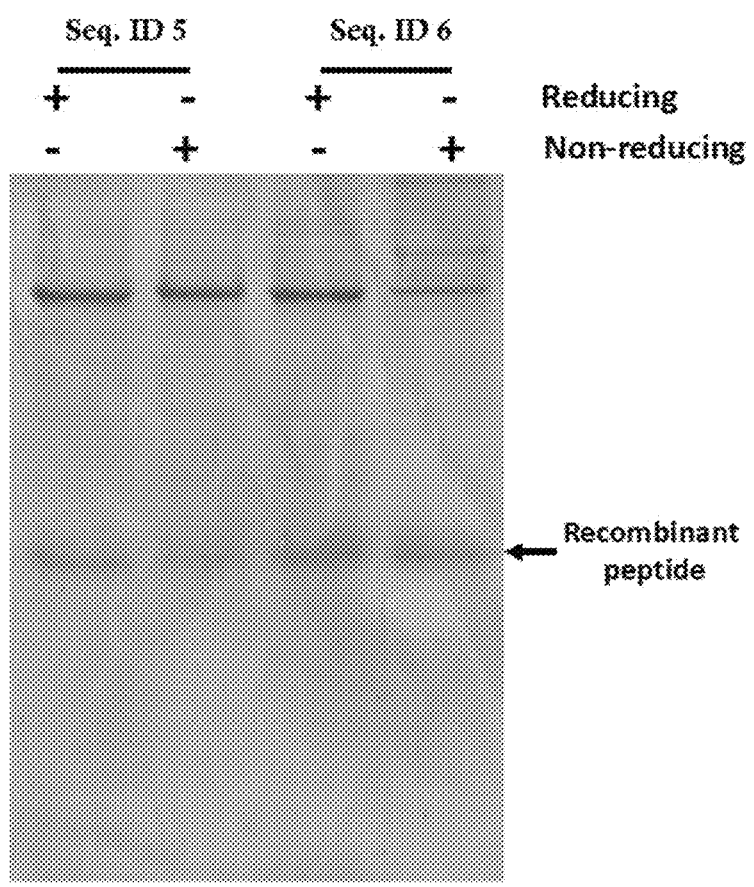
FIG. 6 is pictorial representation of SDS-PAGE gel with media component of bacterial cell culture expressing pBacSec-LC vector having secretory signal sequence comprising of Seq. ID 4 in combination with Seq. ID 5, or Seq. ID 4 in combination with Seq. ID 6 under reducing or non-reducing conditions.

As depicted in FIG. 6, under reducing conditions Seq. ID 5 showed more secretion as compared to non-reducing conditions, which explained that the dimerization due to Cys residue at position 14 of the encoded peptide lead to development of inclusion bodies which decreased under reducing conditions. Therefore, mutation of Cys to Ala at position 14 was bound to be important for secretion, and therefore Seq. ID 6 showed same results under reducing and non-reducing conditions.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention.

I claim:
1. A bacterial expression vector for enhanced secretion of recombinant protein by host bacterial cells,
- wherein the bacterial expression vector consists of SEQ ID: 13;
- wherein said expression vector comprises the DNA sequence encoding amino acid sequence of SEQ ID NO: 12, a secretory signal peptide of the gene ompF (outer membrane porin f), and a DNA sequence of SEQ ID No: 6 encoding a truncated YebF peptide of SEQ ID NO:8; and
- wherein said expression vector provides a yield of recombinant protein of 0.5 g/L in one hour and 5 g/L in six hours.

* * * * *